United States Patent [19]

Bonnet

[11] Patent Number: 4,686,984

[45] Date of Patent: Aug. 18, 1987

[54] CATHETER FOR WIDENING A PUNCTURE CHANNEL

[75] Inventor: Ludwig Bonnet, Knittlingen, Fed. Rep. of Germany

[73] Assignee: Richard Wolf GmbH, Fed. Rep. of Germany

[21] Appl. No.: 710,717

[22] Filed: Mar. 12, 1985

[30] Foreign Application Priority Data

Mar. 15, 1984 [DE] Fed. Rep. of Germany ... 8407894[U]

[51] Int. Cl.$^4$ ............................................. A61M 25/00
[52] U.S. Cl. ..................... 128/343; 604/264; 604/43; 128/DIG. 26
[58] Field of Search ........ 128/343, DIG. 26; 604/264, 265, 266, 270, 280, 283, 43

[56] References Cited

U.S. PATENT DOCUMENTS

| 3,421,509 | 1/1969 | Fiore | 128/343 |
| 3,995,617 | 12/1976 | Watkins et al. | 604/247 |
| 4,405,313 | 9/1983 | Sisley et al. | 604/264 |
| 4,434,797 | 3/1984 | Silander | 128/343 |
| 4,449,532 | 5/1984 | Storz | 128/341 |
| 4,543,087 | 9/1985 | Sommercorn et al. | 604/264 |
| 4,547,194 | 10/1985 | Moorehead | 604/283 |
| 4,552,554 | 11/1985 | Groulch et al. | 604/264 |

Primary Examiner—Gene Mancene
Assistant Examiner—John G. Weiss
Attorney, Agent, or Firm—Hill, Van Santen, Steadman & Simpson

[57] ABSTRACT

For widening puncture channels of the kidney, use is made of catheters increasing by steps in diameter, which are inserted consecutively into the kidney through a puncture channel over a guiding rod. One of the catheters is equipped, beside its central passage, with a guiding passage parallel to the former and intended for a second guiding wire.

8 Claims, 9 Drawing Figures

CATHETER FOR WIDENING A PUNCTURE CHANNEL

BACKGROUND OF THE INVENTION

1. Field of the Invention

The invention relates to a dilating apparatus for widening a puncture channel in the kidney, of the type wherein a series of catheters of increasing diameter are used to widen a puncture channel formed initially with a puncture needle.

2. Description of the Prior Art

For examination of kidneys and for percutaneous removal of kidney stones by means of an operational nephroscope, a puncture channel is first made in the kidney by means of a puncture needle, a guiding wire extending through the needle having its distal extremity left in the channel after withdrawal of the needle and subsequently acting as a guide for a guiding tube comprising a distal stop and intended to guide the first catheter widening the puncture. After the first catheter, the other catheters are guided consecutively over the guiding tube and utilised for additional widening of the puncture channel.

After the puncture channel has been widened, a nephroscope is inserted into the kidney along the guiding wire and the guiding wire is then removed. In some circumstances the nephroscope may be caused by handling actions during stone disintegration to leave the puncture channel accidentally so that it is then very difficult to rediscover the puncture in the kidney without a guiding wire. For this reason, a narrow nephroscope shaft was brought into use beside the existing catheters during catheterising, which is traversed by a second guiding wire which extends beside the catheters and beside the nephroscope during insertion of additional catheters and of the nephroscope and provides a safety feature by virtue of the fact that it may be utilised as a guide for the nephroscope if the first guiding wire were to be pulled accidentally out of the puncture channel of the kidney.

SUMMARY OF THE INVENTION

It is an object of the invention to obtain the same degree of safety without utilisation of a thin additional nephroscope shaft whilst reducing the working period and in simplifying the procedure upon inserting a second guiding wire.

This problem is resolved according to the invention in that in the case of a dilator of the type referred to in the foregoing, the second or another catheter has in addition to its central passage an additional parallel guiding passage for a second guiding or safety wire.

DETAILED DESCRIPTION OF THE PREFERRED EMBODIMENTS

Figure 1:
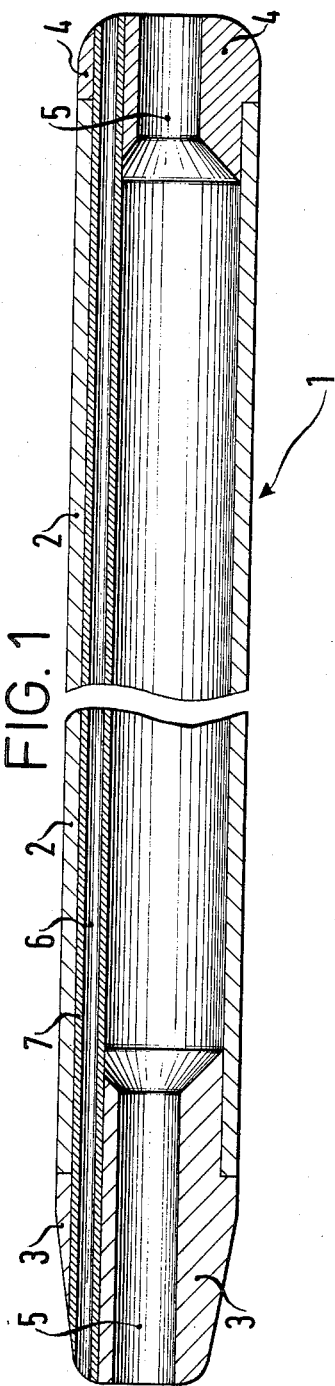
FIG. 1 shows a catheter according to a first embodiment of the invention, in axial longitudinal cross-section.

The catheter 1 according to FIG. 1 has a long cylindrical middle section 2, its two end extremities having terminal elements 3 and 4 inseparably secured to them.

Both the elements 3 and 4 each have a first central passage 5, these being mutually aligned and being widened conically at the two extremities turned towards each other. An additional guiding passage 6 is situated parallel to the first passage 5 and extends almost throughout the length of the catheter, so that the second guiding wire may be inserted in an uncomplicated manner into the nephrostomy channel. The passage 6 comprises a cylindrical tube 7 and may have a comparatively small passage diameter so that the gradiation of the individual catheters with respect to each other need not be altered and that catheters already available may continue to be utilised in conjunction with the catheter according to the invention. The distal element extremity 3 is tapered conically so that the nephrostomy channel may be widened, starting from the catheter of lesser diameter previously inserted therein, to the external diameter of the catheter according to the invention. By contrast, the proximal element extremity 4 has a spheroidal surface to prevent pressure spots in the hand if the catheter is inserted into the nephrostomy channel with comparatively large force needed for dilation.

As variations on the arrangement of FIG. 1, the second guiding passage 6 may also be produced in a different manner, as shown by FIGS. 2 to 6, showing cross-sections of the catheters with correspondingly matchable longitudinal cross-sections.

Figure 2:
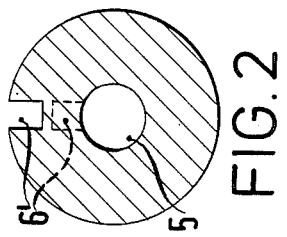

According to FIG. 2, the catheter equipped with the central guiding passage 5 is formed in one piece as compared to FIG. 1, and the additional guiding passage consists of an external longitudinal channel or groove 6' of the dilator wall.

Figure 3:
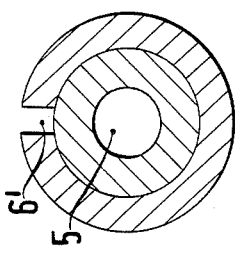

According to FIG. 3, the dialator comprises an inner section having the central passage 5 and a tubular outer tube enclosing the inner section. The outer tube is slotted in longitudinal direction, and this slot forms a groove-shaped guiding passage or channel 6' for the second guiding wire.

Figure 4:
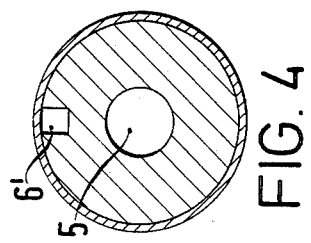
FIGS. 2 to 6 show in transverse cross-section five further embodiments of the invention.
Figure 5:
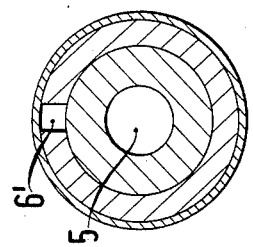

The catheters according to FIGS. 2 and 3 may be enclosed by an outer tube whereby the groove-shaped guiding channels 6' are covered, as illustrated in FIGS. 4 and 5.

Figure 6:
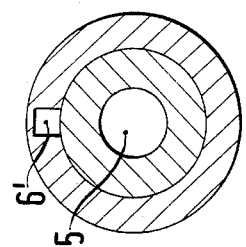

According to FIG. 6 moreover, the inner section comprising the central guiding passage 5 may be surrounded by an unslotted outer tube whose internal surface is endowed with a longitudinally extending groove intended to be a guiding passage 6' for the second guiding wire.

Finally, it is also possible for the second guiding passage to be directly adjacent to the guiding passage 5 as shown in broken lines as 6' in FIG. 2, the externally situated passage 6' then being omitted. The two passages 5 and 6 may then have a common oval shape moreover.

Figure 7:
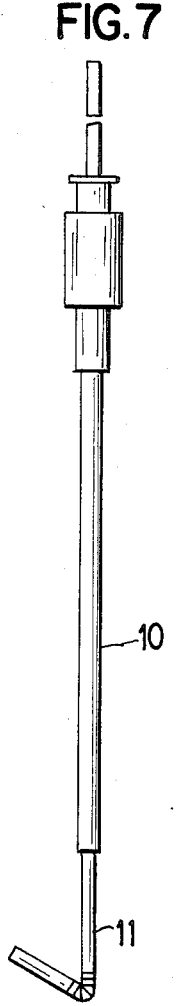
FIG. 7 is a side view of a puncture needle with a first guide wire.
Figure 8:
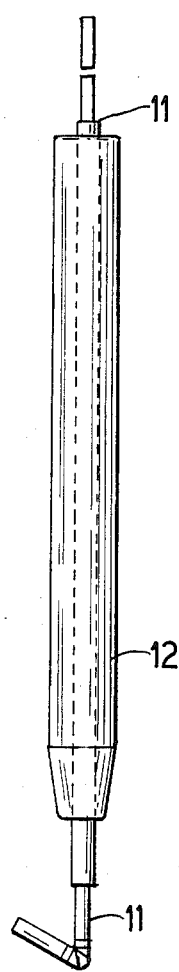
FIG. 8 is a side view of the first guide wire of FIG. 7 with an enlarged catheter or dialator received thereon.
Figure 9:
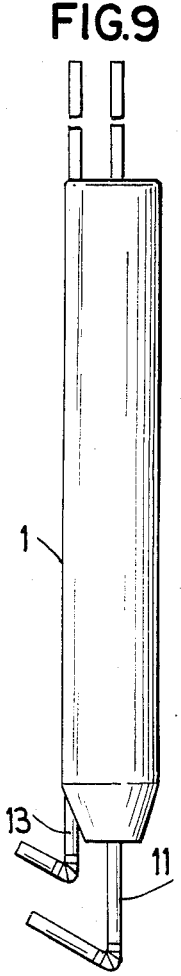
FIG. 9 is a side view of the first guide wire with the catheter of the present invention and a second or additional guide wire.

The operation of the dilating apparatus of the present invention is accomplished by insertion of a puncture needle 10 (FIG. 7) of a known structure into the kidney to form a puncture channel and then passing an end of a first guide wire 11 of a known structure through the needle 10 and into the channel. After inserting the end of the first guide wire 11 into the puncture channel, the needle 10 is removed and the wire 11 remains in place. Then a guide tube 11a is received on the wire and is inserted into the punctured channel with the guide tube 11a substantially having a structure or diameter similar to the needle 10. After inserting the guide tube 11a, a first catheter or dilator 12 is then received on the wire 11 and the guide tube 11a and inserted into the puncture channel to widen the channel. After insertion of the catheter 12 to widen the channel, it is removed and another catheter of increasing diameter is inserted into the channel to continue to increase the size of the channel and the wire 11 and the guide tube 11a are used for guiding these additional catheters until the final size for the catheter is reached. When the final catheter size is reached, the catheter 1 is guided onto the first wire 11 and the tube 11a and into the channel. As illustrated in FIG. 9, a second wire 13 which was inserted along the passage 6, is parallel to the first wire 11 and, thus, also extends into the kidney puncture channel. Then, even after the removal of the first wire 11, the second wire 13 will remain in the channel in case the catheter 1 is accidentally dislodged while passing an instrument through the passage 5 while accomplishing a medical procedure in the interior of the kidney.

What is claimed is:

1. A catheter for widening a puncture channel in a kidney, comprising an elongated body with a tapered end, a second end and a central passage extending between the second end and the tapered end, said body having an additional guiding passage extending between the tapered end and the second end parallel to said central passage for receiving a guide wire.

2. A catheter as claimed in claim 1, wherein said additional guiding passage comprises an external longitudinal groove in the catheter wall.

3. A catheter as claimed in claim 2, wherein said longitudinal groove is covered by a tube enclosing the catheter.

4. A catheter as claimed in claim 1, wherein an inner portion of the catheter having the central passage is surrounded by a tubular outer element with a longitudinal slit having a groove shape and forming said additional guiding passage for the guide wire.

5. A catheter as claimed in claim 4, wherein said guiding passage is covered by a tube enclosing the catheter.

6. A catheter as claimed in claim 4, wherein said longitudinally extending groove-shaped slit extends along an inner surface of the tubular outer element.

7. A catheter as claimed in claim 1, wherein said central passage is formed at the inner extremities of a cylindrical central element by two inserts having respective passages therethrough, said passages widening at their mutually facing ends and wherein the additional guiding passage is formed by a tube extending within and throughout the length of the catheter.

8. Dilating apparatus for widening a puncture channel in a kidney, comprising:
   a puncture needle;
   a first guide wire passing axially through said needle;
   a guide tube adapted to be inserted over said first guide wire and into said puncture channel after removal of the needle thereform;
   a plurality of catheters of different diameters, each having a tapered end and a central axial guide passage dimensioned to fit over said guide tube; and
   a second guide wire;
   wherein at least the catheter of the largest diameter has an additional longitudinal guiding passage parallel to said central passage to receive the second guide wire and position the second guide wire adjacent to the first guide wire.

* * * * *